United States Patent [19]

Scheler et al.

[11] Patent Number: 5,192,640
[45] Date of Patent: * Mar. 9, 1993

[54] PROCESS FOR PREPARING 7-HYDROXY-1,2-NAPHTHOQUINONE-2-DIAZIDE-4-SULFONIC ACID OR SALTS THEREOF

[75] Inventors: Siegfried Scheler, Wiesbaden; Gerhard Buhr, Koenigstein; Klaus Bergmann, Mainz-Bretzenheim, all of Fed. Rep. of Germany

[73] Assignee: Hoechst Aktiengesellschaft, Frankfurt am Main, Fed. Rep. of Germany

[*] Notice: The portion of the term of this patent subsequent to Dec. 3, 2008 has been disclaimed.

[21] Appl. No.: 564,643

[22] Filed: Aug. 9, 1990

[30] Foreign Application Priority Data

Aug. 12, 1989 [DE] Fed. Rep. of Germany ....... 3926774

[51] Int. Cl.$^5$ .................. G03F 7/022; G07C 309/35; G07C 245/12
[52] U.S. Cl. .................... 430/169; 430/168; 534/557; 534/558; 534/564
[58] Field of Search .......... 534/558, 557, 564; 430/168, 169

[56] References Cited

U.S. PATENT DOCUMENTS

| | | |
|---|---|---|
| 2,987,513 | 6/1961 | Schmidt et al. |
| 4,104,070 | 8/1978 | Moritz et al. |
| 4,576,901 | 3/1986 | Stahlhofen et al. ................ 430/325 |
| 5,077,395 | 12/1991 | Scheler et al. ...................... 534/557 |

FOREIGN PATENT DOCUMENTS 3837499 5/1990 Fed. Rep. of Germany .

OTHER PUBLICATIONS

E. L. Martin, et al., "1,2-Naphthoquinone-4-sulfonate, Ammonium and Potassium", *Organic Syntheses*, vol. 3, pp. 633-636.

M. Gates, et al., "The Synthesis and Resolution of 3-Hydroxy-N-methylisomorphinan", *Journal of the American Chemical Society*, vol. 80, Mar., 1958, pp. 1186-1191.

J. Kosar, "o-Quinone Diazides", *Light-Sensitive Systems*, pp. 339-344.

Cava et al., *Journal of the American Chemical Society*, "Condensed Cyclobutane Aromatic Systems. V. The Synthesis of Some alpha-Diazo-indanones: Ring Contraction in the Indane Series", Oct. 1957, pp. 2257-2263.

*Primary Examiner*—Richard L. Schilling
*Assistant Examiner*—Christopher G. Young
*Attorney, Agent, or Firm*—Foley & Lardner

[57] ABSTRACT

A process for preparing 7-hydroxy-1,2-naphthoquinone-2-diazide-4-sulfonic acid or salts thereof, of the general formula Z

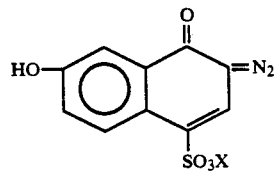

is disclosed in which
X=hydrogen, a metal or an ammonium group, preferably an alkali metal or alkaline earth metal, especially sodium or potassium and the ammonium group.

The compounds can be used as much or as intermediates or starting materials for the production of light-sensitive compounds and radiation-sensitive mixtures and materials.

16 Claims, No Drawings

PROCESS FOR PREPARING 7-HYDROXY-1,2-NAPHTHOQUINONE-2-DIAZIDE-4-SULFONIC ACID OR SALTS THEREOF

BACKGROUND OF THE INVENTION

The present invention relates to a process for preparing 7-hydroxy-1,2-naphthoquinone-2-diazide-4-sulfonic acid or salts thereof. These compounds may be used in the preparation of light-sensitive compounds and radiation-sensitive mixtures.

Esters, amides and hydrazides of 1,2-naphthoquinone-2-diazide-sulfonic acids have been used for many years as light-sensitive compounds for radiation-sensitive mixtures such as, for instance, photoresists for the production of semiconductor components in microelectronics or as coating solutions for the production of photomechanically processable printing forms or color proofing films. Suitable compounds and processing methods have been described in J. Kosar, *Light-Sensitive Systems*, John Wiley & Sons, New York, Chapter 7.4, 1965, U.S. Pat. No. 4,104,070, U.S. Pat. No. 4,576,901 and EP 0,212,482.

The preparation of the 1,2-naphthoquinone-2-diazide-sulfonic acids on which these known derivatives are based starts from 1-naphthol-4-sulfonic acid or 1-naphthol-5-sulfonic acid. The starting material is nitrosated with an alkali metal nitrite in dilute mineral acid. The 2-nitroso-1-naphthol-sulfonic acids formed are isolated, and the unconverted starting materials as well as the by-products formed during the nitrosation are removed by washing out or redissolution. The nitroso compound is then reduced in aqueous solution to the corresponding amino compound The latter is isolated and freed of unconverted starting materials, and of by-products formed, by digestion in water or by redissolution. The amino compound is then suspended in water and diazotized at a pH of 4–6 with an alkali metal nitrite in the presence of Cu(II) salts. In most cases, the 1,2-naphthoquinone-2-diazide-sulfonic acids obtained in this way must still be freed by redissolution or recrystallization from the dark-colored by-products formed in the diazotization.

The disadvantage of this preparation process is essentially that the starting materials unconverted in the individual reaction stages and the by-products formed must be separated from the desired main product by an additional purification step. This entails low yields, a not always satisfactory product quality and high production costs.

EP 0,283,898 discloses a process for preparing benzoquinone-diazide-sulfonic acids and naphthoquinone-diazide-sulfonic acids, which may be substituted by halogen, nitro groups or alkyl groups, and salts thereof. In this case, the starting material is an arylsulfonic acid having at least one hydroxyl group, the acid is nitrosated in a known manner, the nitroso compound formed is reduced in the alkaline pH range and the amino compound is then converted to a sulfamate derivative which is subsequently mixed with a diazotizing agent. After acidification of the mixture, this gives the benzoquinone-diazide-sulfonic acids or naphthoquinone-diazide-sulfonic acids. The reaction products formed after each reaction step are not isolated in between but remain in solution for further reaction ("one-pot reaction"). By-products and impurities arising in the individual process steps can be removed in a satisfactory manner by filtration of the reaction solution.

It is disadvantageous in this one-stage process that the various process steps can be carried out only within a relatively narrow pH range and the reaction times and reaction temperatures must be adhered to very exactly. The end products obtained by this process are as a rule not free of isomeric compounds. A universal industrial use of the compounds prepared by this process is therefore restricted.

In German Patent Application P 38 37 499.4, which is not a prior publication, a process for the preparation of esters of ring-substituted 1,2-naphthoquinone-2-diazide-4-sulfonic acids is described, wherein 1,2-naphthoquinone-2-diazide-4-sulfonic acids, substituted in the 5-, 6-, 7- or 8-position by halogen, alkoxy or alkoxycarbonyl, arise as intermediates.

In this case, the starting material is a correspondingly substituted 2-naphthol which is nitrosated in the 1-position, the product is sulfonated with alkali metal hydrogen sulfite in the 4-position, and the nitroso group is then reduced at a pH of about 7 or less by acidification with a mineral acid to give the amino group. The 2-amino-1-naphthol-4-sulfonic acid is oxidized to the corresponding 1,2-naphthoquinone-4-sulfonic acid, and the latter is reacted with p-toluenesulfonic acid hydrazide in an organic solvent at temperatures of 20°–100° C. to give the corresponding ring-substituted 1,2-naphthoquinone-2-diazide-4-sulfonic acid.

By means of chlorination with chlorosulfonic acid or a chlorosulfonic acid/thionyl chloride mixture, the sulfonic acid chloride is obtained in a known manner, and this is then condensed with a phenolic component to give the corresponding ring-substituted 1,2-naphthoquinone-2-diazide-4-sulfonic acid esters. The individual process steps for preparing the intermediates and end products are known from the literature. The process is dependent on the relatively poor accessibility of the substituted 2-naphthols used as the starting materials. For example, 7-alkoxy-2-naphthol is obtained according to known processes by monoalkylation of 2,7-dihydroxynaphthalene in a yield of only about 50–55% of theory. The yields of the subsequent reaction stages—nitrosation, sulfonation and reduction, oxidation, introduction of the diazo group - are satisfactory. In spite of the omission of additional purification of the intermediate stages, the overall yield of 7-alkoxy-1,2-naphthoquinone-2-diazide-4-sulfonic acid, relative to the 2,7-dihydroxynaphthalene employed, is not yet satisfactory, so that the production costs for the sulfonic acid esters which can be prepared are relatively high.

A further process for preparing ring-substituted 1,2-naphthoquinone-2-diazide-4-sulfonic acids, which can be used for the synthesis of the corresponding esters and amides, is indicated in German Patent Application P 38 37 500.1, which is not a prior publication. For the preparation of 7-methoxy-1,2-naphthoquinone-2-diazide-4-sulfonic acid, the starting material is, for example, commercially-available 1-acetylamino-7-naphthol. The latter can be converted in a 7-stage reaction sequence - methylation of the phenolic hydroxyl group, elimination of the acetyl group and preparation of 1-amino-7-methoxynaphthalene hydrogen sulfate, sulfonation in the 4-position by dry heating ("baking reaction"), replacement of the amino group by a hydroxyl group ("Bucherer reaction"), nitrosation in the 2-position, reduction of the nitroso group to the amino group, and diazotization to the desired compound.

Because of the multi-stage nature of the process, process steps which are difficult to carry out on an industrial scale, and the not always satisfactory yield of individual intermediate stages, this preparation process also raises industrial problems. It is, however, of extreme importance for the production of photoresists to have available an economical synthesis process for the radiation-sensitive components.

DD 263,982 discloses a preparation of 2-diazo-1-oxo-1,2-dihydronaphthalene derivatives, starting from 1,7-dihydroxynaphthalene derivatives. However, the 1,7-dihydroxynaphthalene-4-sulfonic acid used as the starting material for this purpose is not readily available, so that it is extremely expensive to carry out the overall process. Moreover, the diazotization of the amino intermediate is possible in acceptable quality only under defined conditions of pH and temperature and in the presence of heavy metal salts, and only in a low yield.

The esters and amides of 7-methoxy-1,2-naphthoquinone-2-diazide-4-sulfonic acid are, because of the shift of their absorption to longer wavelengths and because of their high reversal potential, outstandingly suitable for use in photoresist layers, which can be structured in the g-line (436 nm) and i-line (365 nm) regions and can be processed either positively or negatively.

SUMMARY OF THE INVENTION

It is therefore an object of the present invention to provide a process for preparing 1,2-naphthoquinone-2-diazide-4-sulfonic acid substituted in the 7-position, and derivatives thereof, which avoids the disadvantages of the known processes, by means of which compounds such as acids, salts and the esters and amides preferred for photoresists can be prepared inexpensively and in a good yield by process steps of simple production technology.

In accordance with these objects, a process is provided for preparing a compound of the formula Z

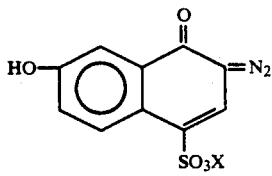

in which

X = hydrogen, a metal or an ammonium group, comprising the steps of:

1) nitrosating 2,7-dihydroxynaphthalene;
2) sulfonating the resulting 2,7-dihydroxy-1-nitrosonaphthalene (I) with an alkali metal hydrogen sulfite and reducing the bisulfite addition compound formed in acidic solution to 2,7-dihydroxy-1-aminonaphthalene-4-sulfonic acid (II);
3) oxidizing the 2,7-dihydroxy-1-aminonaphthalene-4-sulfonic acid to 7-hydroxy-1,2-naphthoquinone-4-sulfonic acid (III) and precipitating this acid as a first salt; and
4) converting this salt with an arylsulfonic acid hydrazide to a salt of 7-hydroxy-1,2-naphthoquinone-2-diazide-4-sulfonic acid (IV), isolating this salt, and optionally converting this salt to the correspondig acid.

The present invention further provides a radiation-sensitive mixture comprising a radiation-sensitive compound prepared by the process, or an ester or amide of this compound.

The present invention also provides a radiation-sensitive material comprising a support and a radiation-sensitive layer comprising a compound prepared by the process or an ester or amide of such a compound.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

According to the present invention, compounds of the general formula Z

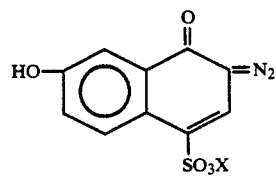

are prepared in which

X = hydrogen, a metal, preferably an alkali metal or alkaline earth metal, especially sodium or potassium, or an ammonium group, which comprises 1) nitrosating 2,7-dihydroxynaphthalene,
2) sulfonating the resulting 2,7-dihydroxy-1-nitrosonaphthalene (I) with an alkali metal hydrogen sulfite and reducing the bisulfite addition compound formed in acidic solution to 2,7-dihydroxy-1-aminonaphthalene-4-sulfonic acid (II),
3) oxidizing the latter to 7-hydroxy-1,2-naphthoquinone-4-sulfonic acid (III) and precipitating it as a salt and
4) converting this salt with an arylsulfonic acid hydrazide to the corresponding salt of 7-hydroxy-1,2-naphthoquinone-2-diazide-4-sulfonic acid (IV) and isolating this salt.

The compounds produced by the process steps are shown in the following reaction diagram.

Reaction diagram

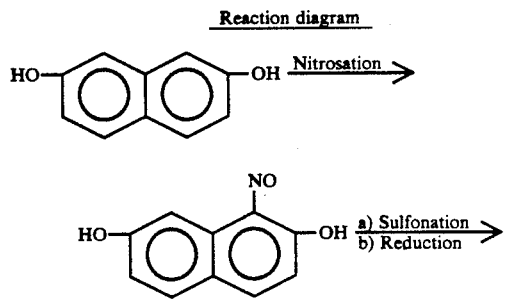

I

-continued
Reaction diagram

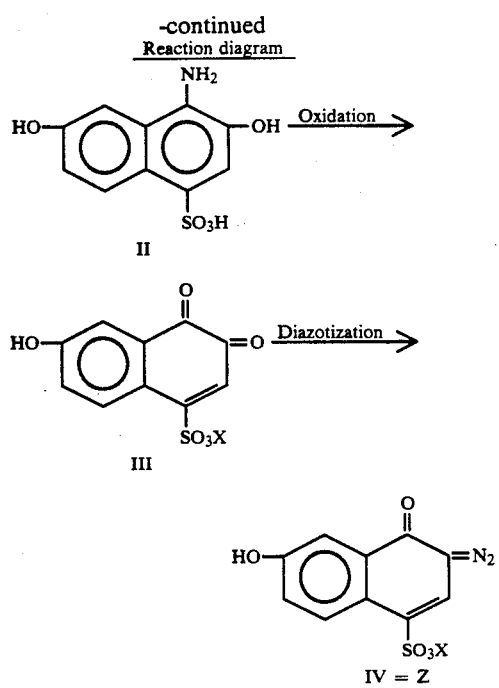

The advantage of the process according to the invention is that there are no additional purification steps for the intermediates which arise.

The nitrosation is preferably carried out in an aqueous suspension containing acetic acid with an alkali metal nitrite at temperatures of about +5° to −10° C. The nitroso compound is then isolated. The sulfonation with an alkali metal hydrogen sulfite or alkali metal disulfite succeeds in aqueous phase in a pH range of about 5–7. The bisulfite addition compound formed is reduced, without intermediate isolation, in an aqueous solution containing a mineral acid at temperatures between about 20° and 60° C. to the corresponding amino compound. The oxidation is preferably carried out with about 15–25% by weight aqueous nitric acid at temperatures between about 15° and 25° C. The naphthoquinone-sulfonic acid formed is preferably precipitated and isolated as the ammonium salt or potassium salt, especially as the potassium salt. The conversion to the diazide is carried out with p-toluenesulfonic acid hydrazide in aqueous or organic phase, preferably in methanol, at temperatures between about 20° and 70° C., preferably between about 25° and 30° C., to give the corresponding salt of 7-hydroxy-1,2-naphthoquinone-2-diazide-4-sulfonic acid, which is then isolated.

The compounds according to the invention can be used as such, but preferably as starting materials via the intermediate of their sulfonic acid chlorides for the production of the corresponding esters or amides, which can be used in radiation-sensitive mixtures or materials.

The preparation process according to the invention starts from commercially-available 2,7-dihydroxynaphthalene which can be converted in a known manner by nitrosation with sodium nitrite at temperatures between about 0° and 5° C., either in an aqueous suspension containing a mineral acid (Clausius, Chem. Ber. 23, 517 (1890); Leonhardt & Co, German Patent 55,204 (1889)) or in a solution containing acetic acid (Kaufler and Bräuer, Chem. Ber. 40, 3275 (1907)), to 2,7-dihydroxy-1-nitrosonaphthalene (I) or the tautomeric 7-hydroxy-1,2-naphthoquinone-1-oxime (I a). By either of the known processes, the yield and quality of the 2,7-dihydroxy-1-nitrosonaphthalene (I) are not satisfactory.

Very surprisingly, however, the nitrosation of 2,7-dihydroxynaphthalene analogously to the method described by Gates and Webb in J. Am. Chem. Soc. 80,1186 (1958), for the preparation of 6-methoxy-1-nitroso-2-naphthol proceeds with almost quantitative conversion and in very good purity. According to this, sodium nitrite is added to a finely disperse suspension of 2,7-dihydroxynaphthalene, obtained by precipitation of 2,7-dihydroxynaphthalene with ice from a warm solution containing acetic acid, with vigorous stirring at about +5° to −10° C. The resulting dark-red microcrystalline nitroso/oxime compound (I/Ia) is filtered off with suction, washed with water until neutral and, if desired, dried. The reaction product obtained by this procedure is further processed without purification, preferably as a product moist with water.

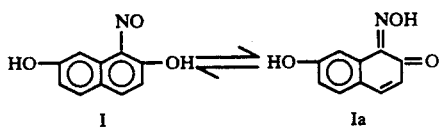

In the second reaction stage, the 2,7-dihydroxy-1-nitrosonaphthalene (I) which is generally still moist with water and which reacts in the tautomeric oxime form (Ia), is first suspended, according to Böninger, Chem. Ber. 27, 3050 (1894), in commercially-available 37% aqueous sodium hydrogen sulfite solution and stirred at about 20°–25° C. until it is completely dissolved. The bisulfite addition compound (IIa) thus formed is not isolated, but the brown reaction solution is acidified with hydrochloric acid and heated to about 25°–60° C. 2,7-Dihydroxy-1-aminonaphthalene-4-sulfonic acid (II) is formed by reduction of the nitroso group and aromatization of the cycloaliphatic ring system. The aminonaphtholsulfonic acid (II) is isolated by filtering off the resulting light-gray crystals with suction, washing these on a suction filter first with water and then with methanol and, if desired, drying them. The reaction product thus prepared is used without further purification, if appropriate still moist, for the next reaction stage. The yield of reaction product II is about 90–95% of theory.

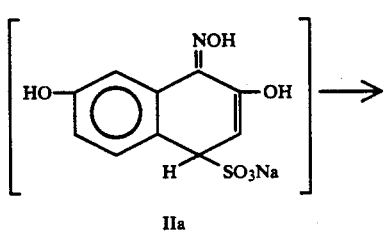

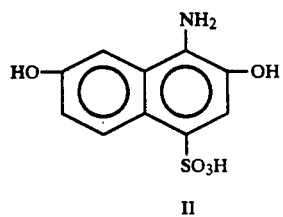

When carrying out the reaction in practice, it is more advantageous to use solid, storage-stable sodium disulfite in place of the commercially-available sodium hydrogen sulfite solution.

In the third reaction stage, 2,7-dihydroxy-1-aminonaphthalene-4-sulfonic acid (II) is oxidized with an oxidizing agent to 7-hydroxy-1,2-naphthoquinone-4-sulfonic acid (III).

Examples of suitable oxidizing agents are potassium peroxydisulfate ($K_2S_2O_8$), Cr(VI) oxide, Pb(IV) oxide, Fe(III) chloride, chlorine, bromine or nitrous acid. Preferably, however, dilute nitric acid is used as the oxidizing agent. The 7-hydroxy-1,2-naphthoquinone-4-sulfonic acid (III) is usually isolated as the ammonium salt or as an alkali metal salt.

When nitric acid is used, the procedure used is advantageously that described by Martin and Fieser in Org. Synth. Coll. Vol. III, 633 (1955). The oxidation takes place preferably at temperatures between about 15° and 25° C., the solid aminonaphthol-sulfonic acid generally being introduced in portions into the nitric acid with stirring. Advantageously, dilute nitric acid is used, in order to maintain the reaction mixture, which is in the form of a suspension, in a state which can be stirred, and in order to be better able to limit the oxidation, which proceeds exothermically, to room temperature by external cooling. A particularly suitable oxidizing agent is 15 to 25% nitric acid, more preferably 18 to 22% nitric acid. The 7-hydroxy-1,2-naphthoquinone-4-sulfonic acid (III) formed is preferably precipitated as the ammonium salt or potassium salt by salting out with ammonium chloride or potassium chloride, respectively, and isolated by filtration. The filter residue is washed with a saturated ammonium chloride or potassium chloride solution and then with ethanol and, if desired, dried at about 20°-40° C. The salts of 7-hydroxy-1,2-naphthoquinone-4-sulfonic acid prepared in this way generally contain small proportions (about 2-3%) of 7-hydroxy-1,2-naphtho-quinone-1-diazide-4-sulfonic acid (IVa). This is formed in a side reaction by diazotization of the 2,7-dihydroxy-1-aminonaphthalene-4-sulfonic acid employed by nitrous acid, which is present in the oxidation medium when nitric acid is used. However, this by-product, formed in only a small quantity, does not interfere with the subsequent conversion to 7-hydroxy-1,2-naphthoquinone-2-diazide-4-sulfonic acid (IV), since the salts of the isomeric 7-hydroxy-1,2-naphthoquinone-1-diazide-4-sulfonic acid (IVa) are more readily soluble than the desired salts of 7-hydroxy-1,2-naphthoquinone-2-diazide-4-sulfonic acid (IV). When nitric acid of higher concentration is used, the proportion of 7-hydroxy-1,2-naphthoquinone-1-diazide-4-sulfonic acid (IVa) increases.

Markedly greater quantities (about 20-40%) of 7-hydroxy-1,2-naphthoquinone-1-diazide-4-sulfonic acid (IVa) are formed by the oxidation method, described by Böninger in Chem. Ber. 27, 3050 (1894), in dilute hydrochloric acid with sodium nitrite at about 0° to 5° C. According to this procedure, the potassium salts of the desired 7-hydroxy-1,2-naphthoquinone-4-sulfonic acid (III) and of the undesired 7-hydroxy-1,2-naphthoquinone-1-diazide-4-sulfonic acid (IVa) are precipitated together from the red-brown solution by salting-out with potassium chloride. A separation of the potassium salts of these two sulfonic acids by fractional crystallization is possible in principle, but involves large losses. This oxidation method is therefore unsuitable for an industrial production process.

In the fourth reaction stage, the ammonium salt or the alkali metal salt, preferably the potassium salt of 7-hydroxy-1,2-naphthoquinone-4-sulfonic acid (III), is converted with an arylsulfonic acid hydrazide, for example, p-toluenesulfonic acid hydrazide, in an aqueous, but preferably alcoholic suspension, for example, in methanol, at temperatures between about 20° and 70° C., preferably between about 20 and 30° C., with high regioselectivity to the corresponding salts of 7-hydroxy-1,2-naphthoquinone-2-diazide-4-sulfonic acid (IV). The isomeric salts, still to be expected, of 7-hydroxy-1,2-naphthoquinone-1-diazide-4-sulfonic acid (IVa) are formed in only extremely small proportions (about 1-2%) under these reaction conditions.

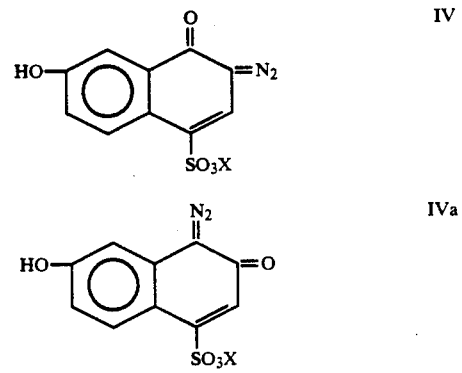

The excellent regioselectivity in this reaction is surprising, inasmuch as the isomer ratio of the o-benzoquinone-diazides prepared by Horner and Dürckheimer and described in Chem. Ber. 95, 1206 (1962), differs in some cases very significantly from the isomer ratio of the above mentioned substituted o-naphthoquinone-diazides. 7-Hydroxy-1,2-naphthoquinone-2-diazide-4-sulfonic acid (IV) and its salts have hitherto not yet been described in the literature. By means of reactions on the phenolic hydroxyl group, for example, alkylation or acylation, or on the sulfonic acid group, for example, chlorination, it is now possible in a very simple manner to prepare the substituted 1,2-naphthoquinone-2-diazide-4-sulfonic acids or 7-hydroxy-1,2-naphthoquinone-2-diazide-4-sulfonic acid chloride.

The replacement of an oxygen atom in α-diketones by the diazo group with an arylsulfonic acid hydrazide is known from the literature as the "Bamford-Stevens reaction." In this reaction, a diketone arylhydrazone is formed as an intermediate, which can be cleaved with or without use of an alkali under very simple and mild reaction conditions to give an o-diazocarbonyl compound.

In DE 1,126,541, this reaction is described for the preparation of 6-nitro-1,2-naphthoquinone-2-diazide-4,8-disulfonic acid from 6-nitro-1,2-naphthoquinone-4,8-disulfonic acid by reaction with an arylsulfonic acid hydrazide and subsequent cleavage of the primarily formed hydrazone in an aqueous alkaline medium. An isolation of the naphthoquinone-diazide derivative as such is not necessary for the preparation process for special azo dyes, described in this application.

A further application of the "Bamford-Stevens reaction" is described by Süs, Steppan and Dietrich in Liebigs Ann. Chem. (1958), for the preparation of polycyclic aromatic o-quinonediazides, for example, phenanthrenequinone-(9,10)-diazide and chrysenequinone- (5,6)-diazide. These o-quinonediazides are obtained by reacting the corresponding polycyclic o-quinones with p-toluenesulfonic acid hydrazide in ethanol at temperatures between 45° and 60° C. and subsequent cleavage of the toluenesulfonic acid hydrazones formed as intermediates, without the use of alkali.

There are summary reports on the range of applications and on the different process variants of the "Bamford-Stevens reaction" in the specialist literature (M. Regitz, *Diazoalkane*, Chapter 5.3, 129 (1977), or Houben-Weyl, *Aromatische Diazoniumsalze*, Volume 10/3, 84).

The procedure in preparing the ammonium salt or potassium salt of 7-hydroxy-1,2-naphthoquinone-2-diazide-4-sulfonic acid (IV) is advantageously such that the corresponding salts of 7-hydroxy-1,2-naphthoquinone-4-sulfonic acid (III) are suspended in water or in a polar organic solvent, preferably methanol, and p-toluenesulfonic acid hydrazide is added with stirring at temperatures between about 15° and 30° C. The reaction mixture is heated to about 20° to 40° C. with continued stirring. When a polar organic solvent, for example, methanol, is used as the reaction medium, the initially dark-red suspension of the salts of 7-hydroxy-1,2-naphthoquinone-4-sulfonic acid changes to a yellow suspension without noticeable dissolution. The ammonium salt or potassium salt of 7-hydroxy-1,2-naphthoquinone-2-diazide-4-sulfonic acid arising in high yields by this procedure is isolated from the reaction mixture by simple filtration and washed with plenty of methanol. Additional purification, for example, reprecipitation or recrystallization, is not necessary.

The use of a polar solvent such as methanol as the reaction medium is particularly advantageous because the resulting ammonium salt or potassium salt of 7-hydroxy-1,2-naphthoquinone-2-diazide-4-sulfonic acid is only very sparingly soluble in this solvent. The small proportions of impurities originating from the starting material and the p-toluenesulfonic acid formed in the hydrazone cleavage are, however, very readily soluble in methanol, so that the yield of pure reaction product is very high in this procedure.

In the aqueous procedure, the yellow suspension formed after the reaction with p-toluenesulfonic acid hydrazide is dissolved by heating to temperatures between about 40° and 50° C., and the yellow-brown solution is freed of small quantities of dark products by means of an adsorbent, for example, activated carbon. The reaction product is precipitated from the clear filtrate by salting out with ammonium chloride or potassium chloride and cooling to about 0° to 5° C. The yield and purity according to this procedure are lower than according to the preferred method in methanol as the reaction medium.

The compounds according to the invention, of the general formula Z, can be used in light-sensitive mixtures or as intermediates for the preparation of esters and amides of 1,2-naphthoquinone-2-diazide-4-sulfonic acids substituted in the 7-position. The esters and amides of these substituted naphthoquinone-diazides can be used as light-sensitive compounds for radiation-sensitive mixtures such as, for example, photoresists for the production of semiconductor components in microelectronics or for coating solutions for the production of photomechanically processable printing forms or color proofing films.

The invention is explained in more detail by the following examples, without limiting it thereto.

2,7-Dihydroxy-1-nitrosonaphthalene (I)

2,7-Dihydroxynaphthalene (BAYER) (250 g=1.56 mol) was dissolved in 875 ml of glacial acetic acid at 0°-90° C. and precipitated again by addition of 2.5 kg of crushed ice. A very finely disperse, light-beige, viscous suspension was formed and the temperature fell to −10° to −12° C. With good stirring and external cooling, 107.88 g (1.56 mol) of solid sodium nitrite were introduced in portions into this suspension, the mixture was stirred for another hour and a further 10.7 g (0.56 mol) of solid sodium nitrite were then added. Stirring was then continued for a further two hours at −8° to −5° C. The 2,7-dihydroxy-1-nitrosonaphthalene formed as dark-red crystals was filtered off with suction and well-pressed on the suction filter. The reaction product, still moist from the suction filter, was then stirred into 5 l of water at 20°-25° C. for about one hour, again filtered off with suction, pressed down well and dried for 24 hours at 20°-25° C. in a circulating-air oven.

Yield: 294 g of pure product (=99.6% of theory)
Characteristic data:
Appearance: dark-red, finely disperse powder
Melting point: 140°-145° C. (brightening) ≧195° C. (charring without melting)
Elemental analysis
Empirical formula: $C_{10}H_7O_3N$
Molecular weight: 189

|  | C | H | N |
|---|---|---|---|
| Calculated: | 63.5 | 3.7 | 7.4 |
| Found: | 63.7 | 3.7 | 7.1 |

2,7-Dihydroxy-1-aminonaphthalene-4-sulfonic acid.2 $H_2O$ (II)

2,7-Dihydroxy-1-nitrosonaphthalene (I) (200 g=1.06 mol) was suspended in 1.75 l of water at 20°-25° C., and 67 g (0.8 mol) of sodium hydrogen carbonate were slowly added in portions with stirring, initial foaming being prevented by addition of 1 ml of n-octanol. Sodium disulfite ($Na_2S_2O_5$) (225 g=1.2 mol) were then added and the mixture was stirred for 17 hours at 20°-25° C., the initially red suspension changing to a brown solution. A small quantity of dark resinous product was then separated off by filtering the solution over activated carbon, 660 ml of 37% strength hydrochloric acid were added to the now clear brown filtrate until the latter was acidic to congo red, and the mixture was heated at 40°-50° C. for 75 minutes with stirring. Part of the reaction product precipitated during this period, with evolution of $SO_2$. After cooling of the reaction mixture to 20°-25° C. and standing for 24 hours, the light-gray crystals which had precipitated were filtered off with suction, pressed down well and washed on the suction filter, first with 500 ml of water and then with 1 l of methanol, until the methanol phase running off showed only a slight yellow color. After drying in a circulating-air oven at 20°-25° C., the 2,7-dihydroxy-1-aminonaphthalene-4-sulfonic acid, which still contained two mol of water of crystallization, was obtained as a light-gray powder.

Yield: 288 g of pure product (=90.5% of theory)
Characteristic data:
Appearance: light-gray powder
Melting point: ≧275° C. (decomposition)
Elemental analysis Empirical formula: $C_{10}H_9O_5NS \cdot 2\,H_2O$
Molecular weight: 291

|             | C    | H   | N   | S    | H₂O  |
|-------------|------|-----|-----|------|------|
| Calculated: | 41.2 | 4.5 | 4.8 | 11.0 | 12.4 |
| Found:      | 41.8 | 4.2 | 4.6 | 10.9 | 12.1 |

7-Hydroxy-1,2-naphthoquinone-4-sulfonic acid (K salt) $\cdot$ 1 H₂O (III)

An amount of 19% nitric acid (219 g=0.662 mol) was cooled to 15° C., and 1.5 g (5.2×10⁻³ mol) of 2,7-dihydroxy-1-aminonaphthalene-4-sulfonic acid . 2 H₂O (II) were introduced with stirring. After starting the oxidation reaction with about 1 ml of 65% nitric acid, the remaining 148.5 g (0.51 mol) of 2,7-dihydroxy-1-aminonaphthalene-4-sulfonic acid . 2 H₂O were then slowly introduced in portions in the course of two hours at 15°-20° C. with continued stirring into the dark-red solution formed. It was possible greatly to reduce the initial foaming by the addition of a few drops of n-octanol. When all of the 2,7-dihydroxy-1-aminonaphthalene-4-sulfonic acid . 2 H₂O had been added, stirring was continued for a further 30 minutes at 15°-20° C. and the dark-red suspension was then stirred into 1.6 l of water at 50° C. This gave a clear dark-red solution. Potassium chloride (170 g) was introduced into this solution in portions of about 25 g each. Even during the addition of the first 25 g of potassium chloride, the precipitation of shiny red crystals from the solution started. The reaction mixture was cooled to 0° to 5° C. and filtered with suction after two hours, and the content of the suction filter was washed first with 80 ml of saturated potassium chloride solution and then with 160 ml of ethanol, and well pressed down. The filter residue was then dried at 20°-25° C. in the circulating-air oven.

The crude 7-hydroxy-1,2-naphthoquinone-4-sulfonic acid (K salt) prepared in this way contained, in addition to potassium chloride, small proportions of 7-hydroxy-1,2-naphthoquinone-1-diazide-4-sulfonic acid (K salt) and 1 mol of water of crystallization.

The pure 7-hydroxy-1,2-naphthoquinone-4-sulfonic acid (K salt) was obtained by reprecipitation of the crude product from water.

| Yield: | 148 g of crude product (89% quality) = 131.7 g of pure product (100% quality), i.e., 82.4% of theory. |
|---|---|

Characteristic data:
Appearance: dark-red, crystalline powder
Melting point: $\geq 275°$ C. (decomposition)
Elemental analysis
Empirical formula: $C_{10}H_5O_6SK \cdot 1\,H_2O$
Molecular Weight: 310

|             | C    | H   | S    | H₂O |     |
|-------------|------|-----|------|-----|-----|
| Calculated: | 38.7 | 2.3 | 10.3 | 5.8 | (%) |
| Found:      | 38.8 | 2.1 | 9.9  | 6.1 | (%) |

7-Hydroxy-1,2-naphthoquinone-2-diazide-4-sulfonic acid (K salt) 1 H₂O (IV)

An amount of 89% pure 7-hydroxy-1,2-naphthoquinone-4-sulfonic acid (K salt) 1 H₂O (131.4g=0.377 mol) was introduced in portions with stirring in the course of 25 minutes into a suspension of 88.2 g (0.47 mol) of p-toluenesulfonic acid hydrazide and 900 ml of methanol. The mixture was stirred for a further 3 hours at 20°-28° C., the dark-red suspension changing to a yellow suspension. The latter was then cooled to 0° to 5° C., the crude yellow reaction product was filtered off with suction and washed twice with 100 ml of ethanol on the suction filter, and the filter residue was dried for 16 hours in a circulating-air oven at 50°-55° C. The crude reaction product contained small proportions of 7-hydroxy-1,2-naphthoquinone-1-diazide-4-sulfonic acid (K salt) and 1 mol of water of crystallization. The pure 7-hydroxy-1,2-naphthoquinone-2-diazide-4-sulfonic acid (K salt) was obtained by reprecipitation of the crude product from ethanol/water.

| Yield: | 112.5 g of crude product (95.2% quality) = 107.1 g of pure product (100% quality). i.e., 93.5% of theory |
|---|---|

Characteristic data:
Appearance: light yellow crystalline powder
Melting point: $\geq 165°$ C. (decomposition)
Elemental analysis
Empirical formula: $C_{10}H_5N_2O_5SK \cdot 1\,H_2O$
Molecular weight 304

|             | C    | H   | N   | S   | H₂O |
|-------------|------|-----|-----|-----|-----|
| Calculated: | 37.3 | 2.2 | 8.7 | 9.9 | 5.6 |
| Found:      | 37.0 | 2.0 | 8.5 | 9.6 | 5.3 |

In Table 1 which follows, some of the compounds according to the invention, of the general formula Z, are exemplified.

| Serial No. | X   | M.p. (°C.)      |       | Elemental analysis |     |      |      |     |
|------------|-----|-----------------|-------|--------------------|-----|------|------|-----|
|            |     |                 |       | C                  | H   | N    | S    | H₂O |
| 1          | K   | $\geq 165$ (dec.) | calc. | 37.3               | 2.2 | 8.7  | 9.9  | 5.6 |
|            |     |                 | found | 37.0               | 2.0 | 8.5  | 9.6  | 6.3 |
| 2          | NH₄ | $\geq 170$ (dec.) | calc. | 42.4               | 3.2 | 14.8 | 11.3 | —   |
|            |     |                 | found | 41.3               | 3.1 | 14.8 | 11.2 | —   |

What is claimed is:

1. A process for preparing a compound of the formula Z

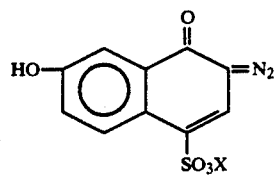

in which X=hydrogen, a metal or an ammonium group, comprising the steps of:
 1) nitrosating 2,7-dihydroxynaphthalene;
 2) sulfonating the resulting 2,7-dihydroxy-1-nitrosonaphthalene (I) with an alkali metal hydrogen sulfite and reducing the bisulfite addition compound formed in acidic solution to 2,7-dihydroxy-1-aminonaphthalene-4-sulfonic acid (II);
 3) oxidizing the 2,7-dihydroxy-1-aminonaphthalene-4-sulfonic acid to 7-hydroxy-1,2-naphthoquinone- 4-sulfonic acid (III) and precipitating this acid as a first salt; and 4) converting this salt with an arylsulfonic acid hydrazide to a salt of 7-hydroxy-1,2-naphthoquinone-2-diazide-4-sulfonic acid (IV), isolating this salt, and optionally converting this salt to the corresponding acid.

2. The process as claimed in claim 1, wherein the nitrosation is carried out in an aqueous suspension containing acetic acid with an alkali metal nitrite at temperatures between about +5° and −10° c., and the nitroso compound is isolated.

3. The process as claimed in claim 1, wherein the sulfonation is carried out with an alkali metal hydrogen sulfite or alkali metal disulfite in aqueous phase in a pH range of about 5 to 7, and the bisulfite addition compound formed is reduced without intermediate isolation in an aqueous solution containing a mineral acid at temperatures between about 20° and 60° C. to the corresponding aminosulfonic acid.

4. The process as claimed in claim 1, wherein the oxidation is carried out with about 15 to 25% by weight aqueous nitric acid at temperatures between about 15° and 25° C., and the naphthoquinonesulfonic acid formed is precipitated and isolated as a salt.

5. The process as claimed in claim 4, wherein the naphthoquinone-sulfonic acid is isolated as the potassium or ammonium salt.

6. The process as claimed in claim 4, wherein the naphthoquinone-sulfonic acid is isolated as the potassium salt.

7. The process as claimed in claim 1, wherein said first salt of the naphthoquinone-sulfonic acid is converted with p-toluenesulfonic acid hydrazide in an organic phase at temperatures between about 20° and 70° C. to said second salt of 7-hydroxy-1,2-naphthoquinone-2-diazide-4-sulfonic acid, and said second salt is isolated.

8. The process as claimed in claim 7, wherein the organic phase comprises a polar organic solvent.

9. The process as claimed in claim 7, wherein the organic phase comprises methanol.

10. The process as claimed in claim 1, wherein X in the formula Z is an alkali metal or alkaline earth metal.

11. The process as claimed in claim 1, wherein the group X in formula Z is selected from the group consisting of sodium, potassium and ammonium.

12. A process as claimed in claim 1, consisting essentially of the recited steps.

13. A process as claimed in claim 1, wherein the nitrosation is carried out by adding sodium nitrite to a finely disperse suspension of 2,7-dihydroxynaphthalene, obtained by precipitation of 2,7-dihydroxynaphthalene with ice from a warm solution containing acetic acid, with vigorous stirring at about 30 5° to −10° C.

14. The process as claimed in claim 13, wherein the sulfonation is carried out with an alkali metal hydrogen sulfite or alkali metal disulfite in aqueous phase in a pH range of about 5 to 7, and the bisulfite addition compound formed is reduced without intermediate isolation in an aqueous solution containing a mineral acid at temperatures between about 20° and 60° C. to the corresponding aminosulfonic acid.

15. The process as claimed in claim 14, wherein the oxidation is carried out with about 15 to 25% by weight aqueous nitric acid at temperatures between about 15° and 25° C. and the naphthoquinone-sulfonic acid formed is precipitated and isolated as a salt.

16. The process as claimed in claim 15, wherein said first salt of the naphthoquinone-sulfonic acid is converted with p-toluenesulfonic acid hydrazide in an organic phase at temperatures between about 20° and 70° C. to said second salt of 7-hydroxy-1,2-naphthoquinone-2-diazide-4-sulfonic acid, and said second salt is isolated.

* * * * *